United States Patent [19]
Tockman et al.

[11] Patent Number: 6,136,021
[45] Date of Patent: Oct. 24, 2000

[54] EXPANDABLE ELECTRODE FOR CORONARY VENOUS LEADS

[75] Inventors: Bruce A. Tockman, Scandia; Randy W. Westlund, Minneapolis; Stuart R. Chastain, Shoreview; Lili Liu, White Bear Lake, all of Minn.

[73] Assignee: Cardiac Pacemakers, Inc., St. Paul, Minn.

[21] Appl. No.: 09/274,621

[22] Filed: Mar. 23, 1999

[51] Int. Cl.[7] .................................................... A61N 1/05
[52] U.S. Cl. ........................ 607/122; 607/119; 607/12.5; 600/381
[58] Field of Search .................................... 600/374, 375, 600/381; 607/122, 125, 126, 119

[56] References Cited

U.S. PATENT DOCUMENTS

| | | |
|---|---|---|
| 4,424,305 | 1/1984 | Gould et al. . |
| 4,434,797 | 3/1984 | Silander . |
| 4,785,059 | 11/1988 | Fydelor et al. . |
| 5,037,427 | 8/1991 | Harada et al. . |
| 5,170,802 | 12/1992 | Mehra ............................. 607/126 |
| 5,234,456 | 8/1993 | Silvestrini . |
| 5,234,457 | 8/1993 | Andersen . |
| 5,242,451 | 9/1993 | Harada et al. . |
| 5,258,042 | 11/1993 | Mehta . |
| 5,259,394 | 11/1993 | Bens .............................. 607/122 |
| 5,445,646 | 8/1995 | Euteneuer et al. . |
| 5,499,994 | 3/1996 | Tihon et al. . |
| 5,571,135 | 11/1996 | Fraser et al. . |
| 5,599,291 | 2/1997 | Balbierz et al. . |
| 5,674,241 | 10/1997 | Bley et al. . |
| 5,860,974 | 1/1999 | Abele ............................. 607/122 |
| 5,951,597 | 9/1999 | Westlund et al. ................ 607/126 |
| 5,954,761 | 9/1999 | Machek et al. ................. 600/375 |

*Primary Examiner*—Carl H. Layno
*Attorney, Agent, or Firm*—Nikolai, Mersereau & Dietz, P.A.

[57] ABSTRACT

Expandable electrodes for intravascular leads permit the electrodes to be placed and retained in the vasculature of the left side of the heart. Such electrodes can be in the form of a balloon, an expandable wire coil, or other expandable shapes.

18 Claims, 6 Drawing Sheets

EXPANDABLE ELECTRODE FOR CORONARY VENOUS LEADS

FIELD OF THE INVENTION

This invention relates to electrodes for cardiac rhythm management devices such as heart pacemakers and defibrillators. More specifically, this invention relates to electrodes intended to be positioned and retained within one of the cardiac veins in contact with the wall of the vein.

BACKGROUND OF THE INVENTION

In recent years it has been determined that various cardiac rhythm anomalies can be effectively treated by applying electrical stimulation pulses to the left side of the heart. In order to provide stimulation pulses to the left side of the heart, it is generally necessary to position an electrode accordingly. Initial efforts to place such an electrode involved highly invasive and traumatic surgery. This surgery required that the chest wall be opened and that an epicardial electrode be sewn or otherwise attached to the heart.

More recently intravascular leads have been developed. The electrode of these leads can be brought into contact with the left side of the heart by advancing the lead through the vena cava, right atrium and coronary sinus into the great vein of the heart. Once there, the electrode can be further advanced toward the apex of the left ventricle through one of the veins that descend from the great vein. See, for example, U.S. Pat. Nos. 5,803,928,; 5,755,766; and 5,755,765 and assigned to Cardiac Pacemakers, Inc.

Leads of the type described in the aforementioned '928, '766 and '765 patents offer significant advantages. Such leads provide a suitable electrical path for delivery of pulses from the cardiac rhythm management device to the left side of the heart. Such leads are also capable of sensing electrical signals otherwise associated with the left side of the heart and transferring these signals back to the cardiac rhythm management device. More importantly, these leads can be placed without the patient receiving the trauma associated with placing a patch electrode on the exterior of the heart.

The efficacy of leads described in the '928, '766 and '765 patents can be enhanced by providing means for ensuring that the electrode associated with the distal end of the lead remains in contact with the vessel wall. Providing a suitable means for ensuring such consistent contact is not easily achieved. The path the lead follows is circuitous and narrow requiring that the lead be very small in diameter and very flexible. Use of a traditional lead fixation device diminishes the flexibility of the lead and increases its diameter. Also, traditional lead fixation devices include tines or other projections which could interfere with advancement of the lead through the vasculature or even damage the vessel wall. Further, sometimes it is necessary to explant a lead for various medical reasons. Thus, the fixation device should be designed to permit the lead to be extracted.

SUMMARY OF THE INVENTION

One object of the present invention is to provide, for use with a cardiac rhythm management device, a lead having an electrode which can be positioned within the vasculature of the heart.

A second object of the invention is to provide such a lead having an electrode which can be positioned in a coronary vein.

A third object of the invention is to provide a lead having an electrode which can be positioned in one of the cardiac veins that descends from the great vein toward the apex of the heart.

A fourth object of the present invention is to provide an adaptable electrode which is designed to hold itself in contact with the vein wall.

A fifth object of the invention is to provide an adaptable electrode which has a reduced diameter during insertion of the lead and then expands into contact with the vein wall once positioned.

A sixth object of the present invention is to provide an adaptable electrode which is of a size and shape and has sufficient flexibility so that it can pass through a circuitous path having a small diameter.

A seventh object of the invention is to provide an adaptable electrode which can be manipulated to permit extraction of the lead if desired.

These and other objects are achieved by the present invention which provides an electrode and means which cooperate with the electrode to cause the diameter of the electrode to expand and establish firm contact with the vein wall. In one embodiment the electrode is in the form of a mechanical inflation balloon. The balloon contains an osmotically activated material and perforations to allow for the ingress of body fluids into the balloon. As body fluids are commingled with the osmotically activated material, the balloon expands bringing the electrode into contact with the vessel wall.

In a second embodiment, the electrode is a coiled conductive member coupled to a constraining mechanism. When the electrode has been properly positioned, the constraining mechanism is removed so that the coil expands. The constraining mechanism can, for example, be made of a dissolvable material such as mannitol. When the material is dissolved by body fluids, the electrode expands into contact with the vessel wall. The constraining mechanism can also be a sleeve which can be mechanically removed once the electrode is in position.

Other preferred embodiments, features and characteristics of the invention will become apparent from the following detailed description of the invention.

DETAILED DESCRIPTION OF THE PREFERRED EMBODIMENTS

Figure 1:
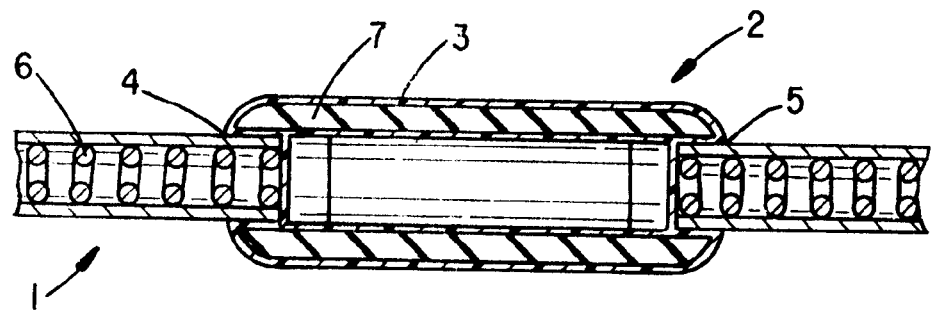
FIG. 1 is a cross-sectional view of an electrode incorporating an expandable balloon in the retracted position.
Figure 2:
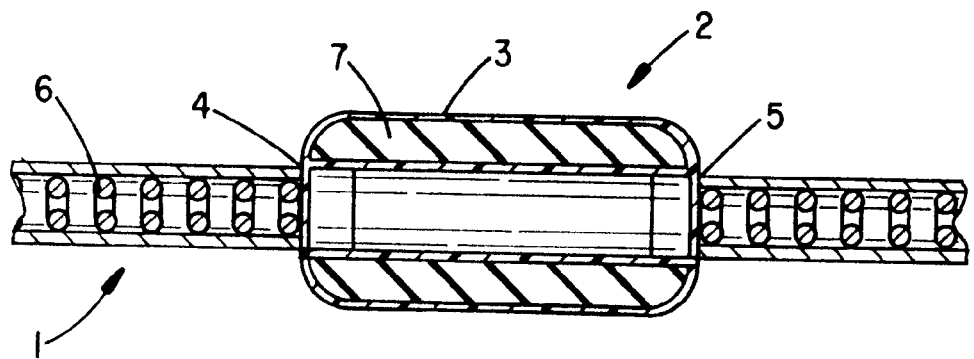
FIG. 2 is a cross-sectional view of the electrode of FIG. 1 with the balloon expanded.
Figure 3:
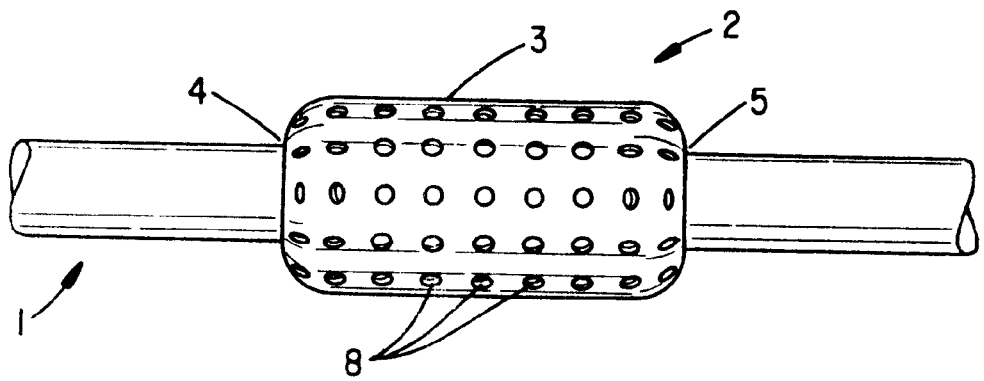
FIG. 3 is a side view of the electrode shown in FIGS. 1 and 2 with the balloon expanded and showing the perforations through the balloon wall to permit the ingress of body fluids.

FIGS. 1–3 show a first embodiment of the invention. As shown, this embodiment includes an elongated lead body 1 and an electrode 2. The electrode 2 is in the form of a balloon 3 coupled at its proximal end 4 and its distal end 5 to the lead body 1. So that it can conduct electricity, the balloon 3 is made of a polymer such as polytetrafluoroethylene and coated with a conductive material by vapor deposition or other means for depositing a thin conductive layer on a polymer substrate. The balloon 3 is also coupled to a conductive coil 6 which extends from the proximal end of the lead past the balloon electrode 3 to provide a conductive path from the balloon electrode 3 to the proximal end of the lead.

The balloon 3 is filled with an inflation material which expands when it comes into contact with body fluids. Suitable materials will typically comprise a hydrophilic polymer that may be treated by a pharmacological, osmotically active agent. For example, the inflation material could be silicone rubber interlaced with sodium chloride, glycerol or any other non-toxic, water soluble material that does not adversely affect the curing of the water permeable polymer (silicone rubber). Silicone rubber is known for its hydrophilic characteristics. Likewise, the presence of an osmotically active agent will cause body fluids to penetrate the balloon 3 and come into contact with the silicone rubber. Body fluids enter the balloon 3 through the orifices such as 8 shown in FIG. 3. Once the electrode 3 is exposed to the body fluids, the body fluids enter the orifices 8 to expand the balloon 3 by activation of the osmotic agent within the hydrophilic material 7 until the balloon electrode 3 comes into contact with the vessel wall.

A second embodiment of the present invention is shown in FIGS. 4–7. These figures show an elongated lead body 1 and an electrode 2. The electrode in this embodiment is an expandable coil 3 coupled at its proximal end 4 to the coil 6 that runs from the electrode 2 to the proximal end of the lead. As in the first embodiment, an insulative material covers the conductive coil 6.

Figure 4:
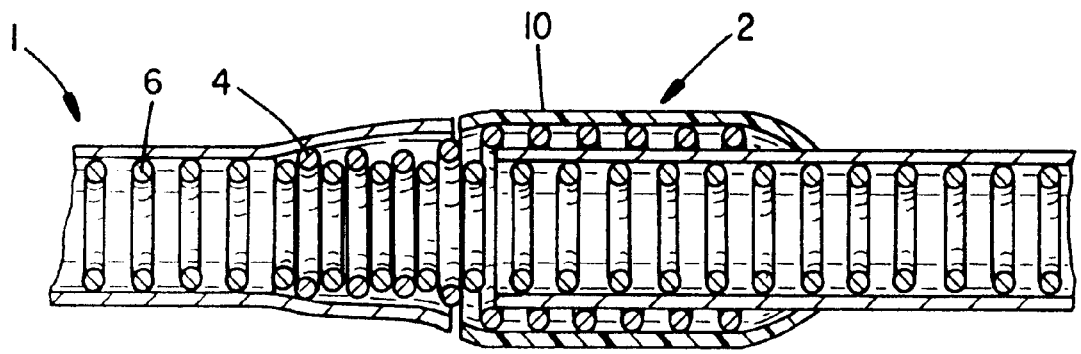
FIG. 4 is a cross-sectional view of an expandable electrode retained by a dissolvable sleeve.
Figure 5:
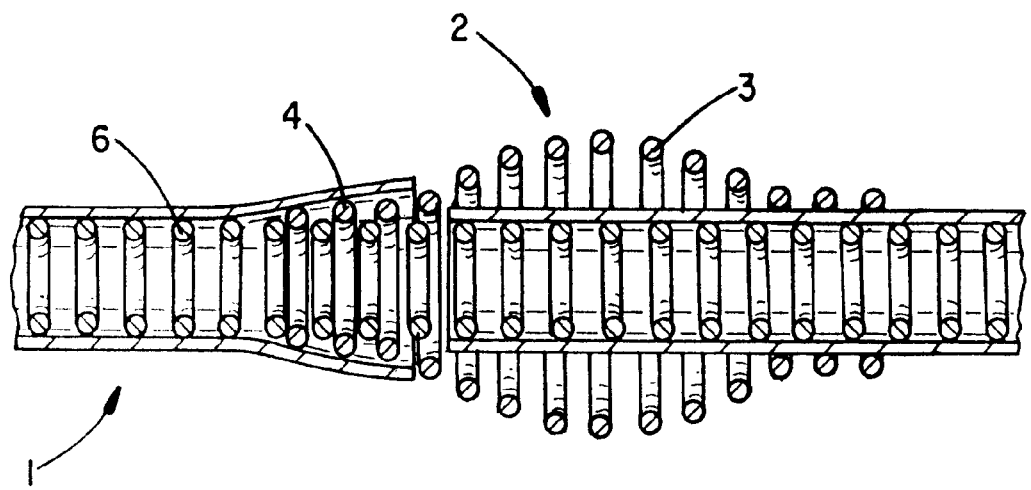
FIG. 5 is a cross-sectional view of the electrode of FIG. 4 after the sleeve is dissolved.
Figure 6:
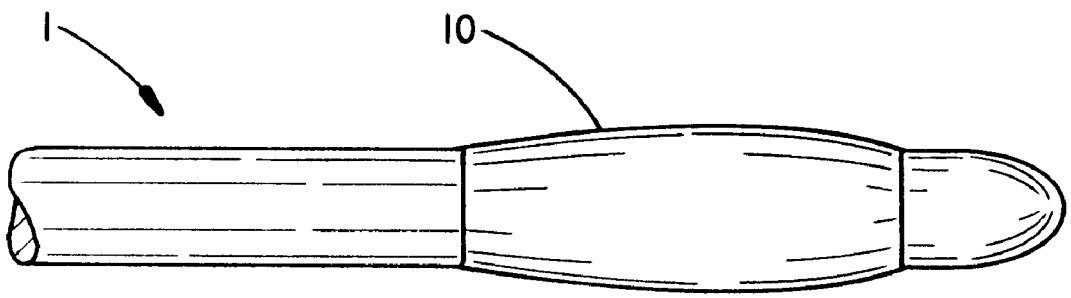
FIG. 6 is a perspective view of the lead shown in FIGS. 4 and 5 with the restraining sleeve in place.
Figure 7:
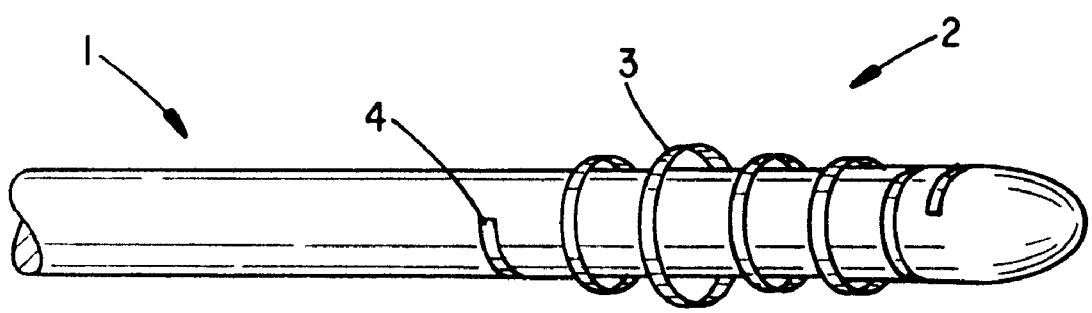
FIG. 7 is a perspective view of the lead shown in FIGS. 4-6 with the restraining sleeve removed.

FIG. 4 also shows a retaining sleeve 10 covering the expandable coil 3. The retaining sleeve 10 is provided to restrict the diameter of the expandable coil 3 until the lead is properly positioned. The sleeve 10 can then be mechanically removed. Alternatively, the sleeve 10 is made of a material that is dissolved by body fluids such as mannitol After the sleeve 10 is removed, either mechanically or as a result of being dissolved by body fluids, the coil 3 will expand to the shape shown in FIG. 5 and into firm, fixed contact with the vessel wall.

Figure 8:
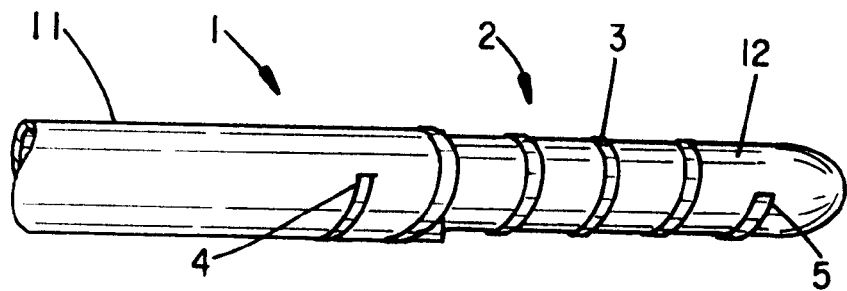
FIG. 8 is a side view of the third alternative lead with the electrode collapsed.
Figure 9:
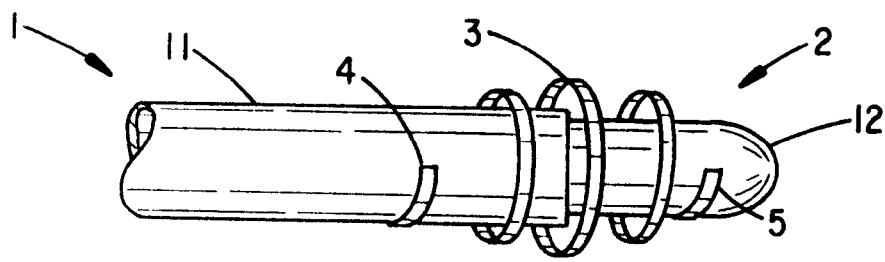
FIG. 9 is a side view of the third alternative lead with the electrode expanded.

FIGS. 8 and 9 show another embodiment including a lead body 1 and electrode 2. The lead body 1 incorporates an outer member 11 and an inner member 12 that projects past the outer member 11 to form a tube within a tube arrangement. The electrode 2 is a coil 3 coupled at its distal end 5 to the inner member 12 and at its proximal end 4 to the outer member 11. A comparison of FIGS. 8 and 9 show that the coil 3 can be expanded or retracted by sliding the outer member 11 over the inner member 12. As the outer member 11 is slid distally over the inner member, the coil 3 expands as shown in FIG. 9. As the outer member is slid proximally over the inner member, the coil retracts as shown in FIG. 8.

Figure 10:
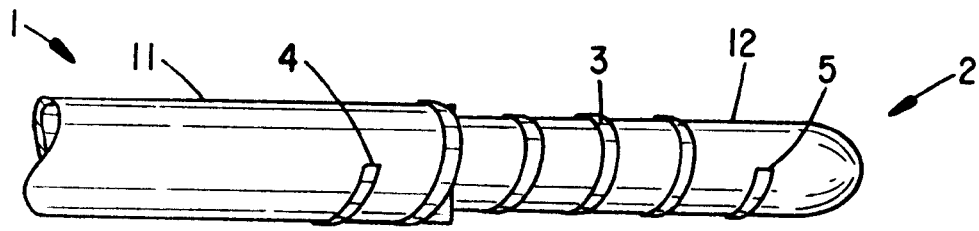
FIG. 10 is a side view of a fourth alternative embodiment with the electrode collapsed.
Figure 11:
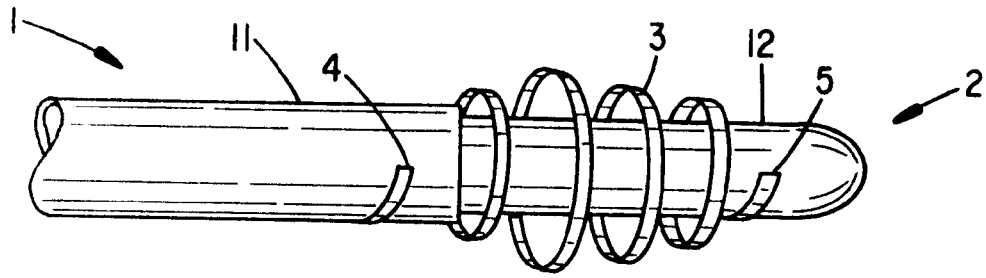
FIG. 11 is a side view of the lead shown in FIG. 10 with the electrode expanded.

The embodiment shown in FIGS. 10 and 11 is similar to that shown in FIGS. 8 and 9. Instead of the outer member 11 sliding over the inner member 12, the inner member and outer member are rotated with respect to each other. When rotated in one direction, the coil 3 expands to the position shown in FIG. 11. When rotated in the opposite direction, the coil 3 retracts to the position shown in FIG. 10.

Figure 12:
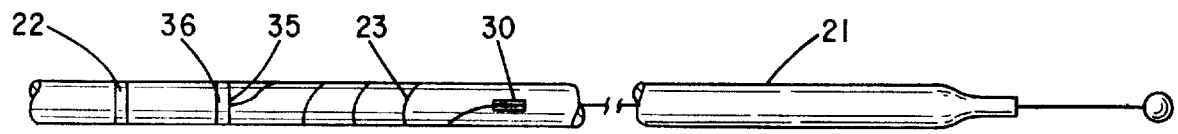
FIG. 12 is a side view of a fifth embodiment with the electrode collapsed.
Figure 13:
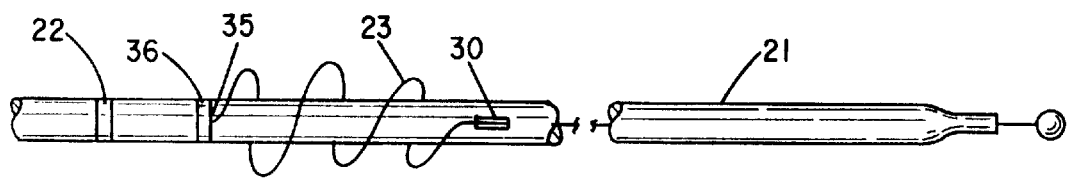
FIG. 13 is a side view of the lead shown in FIG. 12 with the electrode expanded.
Figure 14:
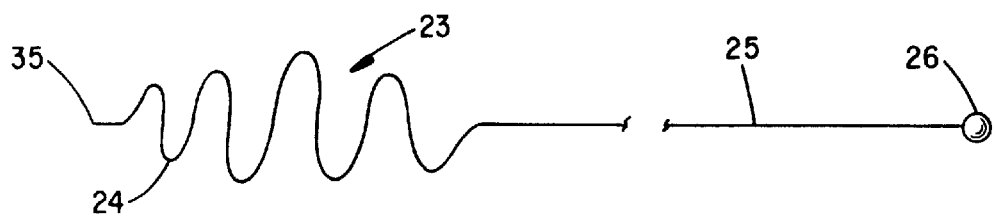
FIG. 14 is a side view of the electrode of the lead shown in FIGS. 12 and 13.

FIGS. 12–14 show the preferred embodiment of a lead having a bipolar configuration incorporating a lead body 21, a first ring electrode 22 of a standard configuration and an adaptable electrode 23. The adaptable electrode 23 includes a coiled section 24, an elongated section 25 and an actuation member 26. When assembled, the adaptable electrode is positioned so that the elongated section 25 is positioned within a lumen (not shown) of the lead body 21 so that the actuation member 26 extends from the proximal end of the lead body and the coiled section 24 extends out of the lead body 21 through an orifice 30 that extends from the lumen to the exterior of the lead. The distal end 35 of the coiled section 24 can be fixed to the lead body 21 by a ring 36. Thus, by pulling on the actuation member 26 one can retract the coil into the position shown in FIG. 12. By pushing the actuation member 26 one can extend coil 23 to assume the expanded helix position shown in FIG. 13. Both the ring electrode 22 and the coil electrode 23 can be coupled to the cardiac rhythm management device to provide bipolar therapy via the lead. Alternatively, one electrode can be used for sensing while the other is used for applying therapeutic stimulations to the heart.

Figure 15:
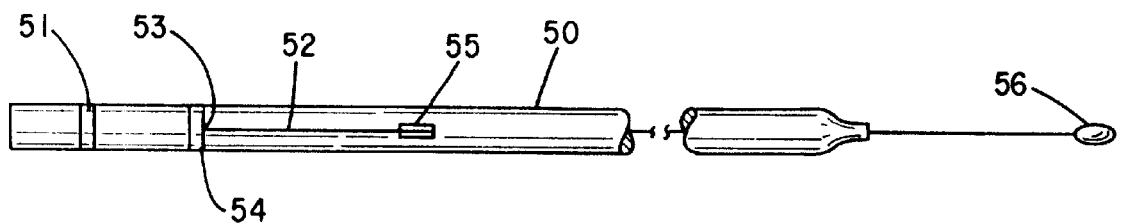
FIG. 15 is a side view of a sixth embodiment with the electrode collapsed.
Figure 16:
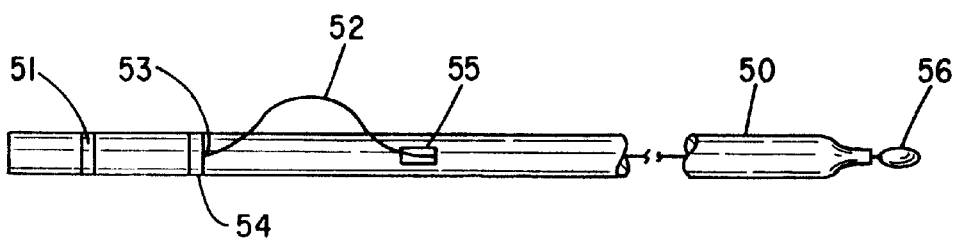
FIG. 16 is a side view of the lead shown in FIG. 15 with the electrode expanded.

Another bipolar lead configuration incorporating the present invention is shown in FIGS. 15 and 16. In this embodiment the lead consists of a lead body 50, a ring electrode 51 and an elongate electrode 52. The elongate electrode 52 is attached at its distal end 53 to a ring 54 and passes through an orifice 55 through a lumen (not shown) and extends past the proximal end of the lead. The proximal end of the elongate electrode 52 is coupled to an actuation member 56. Pulling on the actuation member 56 causes the elongate lead to assume the position shown in FIG. 15. Pushing the actuation member causes the lead to assume the position shown in FIG. 16 and engage the vessel wall into which the lead is inserted.

The coil 3 can be constructed in a number of different ways. It can be formed of a round wire, a ribbon-shaped wire, a coil consisting of a plurality of wires, a braided cable or the like. The coil 3 can also be coated with a hydrophilic coating, polytetrafluoroethylene (PTFE), or silicone. A variety of materials can be used for the coil 3, but the preferred material is nickel-titanium.

The foregoing description of various embodiments has been provided to comply with disclosure requirements of the patent laws. This disclosure is not intended to be limiting. Instead, the scope of the invention is defined by the following patent claims which are to be interpreted to include a full range of equivalents.

What is claimed:

1. A cardiac lead positionable within the vasculature of the heart for use in conjunction with a cardiac rhythm management device, said cardiac lead comprising:

a. a lead body;

b. a balloon electrode having a first retracted position and a second expanded position in which said balloon electrode is in contact with a vessel wall when the lead is positioned within the vasculature of the heart; and c. a water-perineable material within the balloon electrode that reacts with body fluids to cause the balloon electrode to expand by the osmotic process for causing said balloon electrode to move from said first retracted position to said second extended position.

2. The cardiac lead of claim 1 wherein said balloon electrode has perforations which allow body fluids to penetrate the balloon electrode.

3. The cardiac lead of claim 1 wherein said water permeable material includes silicone rubber and wherein said osmotic agent includes a material selected from a group consisting of sodium chloride, glycerol, dexamethasone, sodium phosphate or potassium chloride.

4. The cardiac lead of claim 3 wherein said osmotic agent comprises a pharmacological agent.

5. The lead of claim 1 wherein said water-permeable material is hydrophilic.

6. The lead of claim 1 wherein said water-permeable material includes a hydrophilic substance treated with an osmotically active agent.

7. A cardiac lead positionable within the vasculature of the heart for use in conjunction with a cardiac rhythm management device, said cardiac lead comprising:

a. a lead body;

b. a ribbon wire coil electrode having a first retracted position and a second expanded position in which said electrode is in contact with a vessel wall when the lead is positioned within the vasculature of the heart; and c. adaptation means for causing said electrode to move from said first retracted position to said second extended position.

8. A cardiac lead positionable within the vasculature of the heart for use in conjunction with a cardiac rhythm management device, said cardiac lead comprising:

a. a lead body;

b. a nickel-titanium coil electrode having a first retracted position and a second expanded position in which said electrode is in contact with a vessel wall when the lead is positioned within the vasculature of the heart; and c. adaptation means for causing said electrode to move from said first retracted position to said second extended position.

9. A cardiac lead positionable within the vasculature of the heart for use in conjunction with a cardiac rhythm management device, said cardiac lead comprising:

a. a lead body;

b. a coil electrode having a first retracted position and a second expanded position in which said electrode is in contact with a vessel wall when the lead is positioned within the vasculature of the heart; and c. an outer member that surrounds a portion of the lead body said lead body extending beyond said outer member and said coil electrode coupled to said lead body and said outer member for causing said coil electrode to move from said first retracted position to said second extended position.

10. The cardiac lead of claim 9 wherein said electrode moves between said first retracted position and said second extended position by sliding the outer member relative to the lead body.

11. The cardiac lead of claim 9 wherein said electrode moves between said first retracted position and said second extended position by rotating the outer member relative to the lead body.

12. A cardiac lead positionable within the vasculature of the heart for use in conjunction with a cardiac rhythm management device, said cardiac lead comprising:

a. a lead body;

b. a round or ribbon wire NiTi coil electrode having a first retracted position and a second expanded position in which said electrode is in contact with a vessel wall when the lead is positioned within the vasculature of the heart; and c. adaptation means for causing said coil electrode to move from said first retracted position to said second extended position.

13. A cardiac lead positionable within the vasculature of the heart for use in conjunction with a cardiac rhythm management device, said cardiac lead comprising:

a. a lead body included a lumen and an orifice extending between the lumen and the exterior of the lead;

b. an electrode having a first retracted position and a second expanded position in which said electrode is in contact with a vessel wall when the lead is positioned within the vasculature of the heart; and c. adaptation means for causing said electrode to move from said first retracted position to said second extended position.

14. The cardiac lead arrangement of claim 13 wherein said electrode has a distal end fixed to the exterior of said lead body and extends through said orifice into said lumen.

15. The cardiac lead arrangement of claim 14 wherein said electrode is comprised of coil or braided cable.

16. The cardiac lead arrangement of claim 14 wherein said adaptation means includes a member coupled to said electrode extending from the lead so that one can apply a force to said member to cause the lead to move between said retracted and extended positions.

17. The cardiac lead arrangement of claim 16 wherein said member coupled to said electrode is a coil of round or ribbon wire.

18. The cardiac lead arrangement of claim 17 wherein said coil is coated with a coating selected from a group consisting of polytetrafluoroethylene, silicone, and any other hydrophilic material.

* * * * *